United States Patent
Olson et al.

(10) Patent No.: US 10,123,534 B2
(45) Date of Patent: Nov. 13, 2018

(54) COMPOSITION FOR DETECTION AND TREATMENT OF BED BUGS

(71) Applicants: Ecolab USA Inc., St. Paul, MN (US); Regents of the University of Minnesota, Minneapolis, MN (US)

(72) Inventors: Joelle F. Olson, Shoreview, MN (US); Stephen A. Kells, St. Paul, MN (US); Leonard M. Ver Vers, Downers Grove, IL (US); Roger D. Moon, St. Paul, MN (US); Yvonne M. Killeen, South St. Paul, MN (US)

(73) Assignees: Ecolab USA Inc., St. Paul, MN (US); Regents of the University of Minnesota, Minneapolis, MN (US)

( * ) Notice: Subject to any disclaimer, the term of this patent is extended or adjusted under 35 U.S.C. 154(b) by 187 days.

(21) Appl. No.: 14/733,233

(22) Filed: Jun. 8, 2015

(65) Prior Publication Data
US 2015/0366210 A1    Dec. 24, 2015

Related U.S. Application Data

(60) Provisional application No. 62/110,924, filed on Feb. 2, 2015, provisional application No. 62/014,534, filed on Jun. 19, 2014.

(51) Int. Cl.
*A01N 41/12*    (2006.01)
*A01M 1/02*    (2006.01)
(Continued)

(52) U.S. Cl.
CPC ............. *A01N 41/12* (2013.01); *A01M 1/02* (2013.01); *A01M 1/023* (2013.01); *A01M 1/026* (2013.01);
(Continued)

(58) Field of Classification Search
CPC ........ A01M 1/02; A01M 1/023; A01M 1/026; A01M 1/103; A01M 1/2011; A01N 41/12; A01N 33/08
See application file for complete search history.

(56) References Cited

U.S. PATENT DOCUMENTS 1,259,911 A     3/1918  Seibert
3,484,374 A  *  12/1969 Cyba .................... C08F 8/40
                                              508/224
(Continued)

FOREIGN PATENT DOCUMENTS

CA         2130375 A1    4/1995
CN        202026723      11/2011
(Continued)

OTHER PUBLICATIONS

Adler et al., Modified Atmospheres. In: Alternatives to pesticides in stored-product IPM, (edited by Subramanyam and Hagstrum), Kluwer Academic Publishers, Boston, pp. 105-146 (2000).
(Continued)

*Primary Examiner* — Michael H Wang
(74) *Attorney, Agent, or Firm* — Merchant & Gould P.C.

(57) ABSTRACT

The present disclosure provides for a composition and method for attracting bed bugs to a trap or to a location where an insecticide or pesticide is present, or to a trap or a location where a bed bug infestation can be detected. The present disclosure provides for a composition for attracting bed bugs that includes one or more of methyl diethanolamine (MDEA), monoethanolamine (MEA), diethanolamine (DEA), triethanolamine (TEA), and dimethyl trisulfide (DMTS); a carrier; and optionally one or more amides selected from oleamide, octanamide, nonanamide, and laurylamide; urea, biuret, or triuret; and one or more aliphatic fatty acids. The present disclosure further provides for a method for treating an article by applying the compo-
(Continued)

sition to the article, where the article comprises a device for trapping or detecting bed bugs or a device for treating a bed bug infestation.

33 Claims, 15 Drawing Sheets

(51) Int. Cl.
   *A01M 1/20*     (2006.01)
   *A01M 1/22*     (2006.01)
   *A01M 1/10*     (2006.01)
   *A01M 1/14*     (2006.01)
   *A01N 33/08*    (2006.01)

(52) U.S. Cl.
   CPC .............. *A01M 1/103* (2013.01); *A01M 1/14* (2013.01); *A01M 1/2011* (2013.01); *A01M 1/223* (2013.01); *A01N 33/08* (2013.01); *Y02A 50/374* (2018.01)

(56) References Cited

U.S. PATENT DOCUMENTS

| | | | |
|---|---|---|---|
| 4,217,722 A | 8/1980 | McMullen | |
| 4,709,504 A | 12/1987 | Andric | |
| 4,800,671 A | 1/1989 | Olson et al. | |
| 4,862,638 A | 9/1989 | Stevenson | |
| 5,102,662 A * | 4/1992 | Gallagher | A61K 9/146 |
| | | | 424/405 |
| 5,119,586 A | 6/1992 | Townsend | |
| 5,438,792 A | 8/1995 | Monett et al. | |
| 5,454,186 A | 10/1995 | Gang | |
| 5,597,599 A | 1/1997 | Smith et al. | |
| 6,063,418 A | 5/2000 | Sugimoto et al. | |
| 6,106,821 A * | 8/2000 | Baker | A01N 25/006 |
| | | | 424/405 |
| 6,696,424 B1 * | 2/2004 | Wheeler | A61K 9/1272 |
| | | | 424/450 |
| 6,766,612 B1 | 7/2004 | Liu | |
| 6,814,956 B2 | 11/2004 | Besser et al. | |
| 7,444,711 B2 | 11/2008 | Garcia et al. | |
| 7,910,056 B2 | 3/2011 | Ivanine et al. | |
| 8,146,290 B1 | 4/2012 | Telly | |
| 8,282,952 B2 | 10/2012 | Smit | |
| 8,413,370 B2 | 4/2013 | Messian | |
| 8,661,728 B2 * | 3/2014 | Borth | G01N 33/68 |
| | | | 43/124 |
| 8,789,309 B2 | 7/2014 | Fabry | |
| 8,808,721 B2 * | 8/2014 | Banfield | A01M 1/026 |
| | | | 424/405 |
| 8,931,206 B2 | 1/2015 | Olson et al. | |
| 8,966,812 B2 * | 3/2015 | McKnight | A01M 1/023 |
| | | | 43/107 |
| 9,901,088 B2 | 2/2018 | Backmark et al. | |
| 2003/0033965 A1 | 2/2003 | Van Lint | |
| 2004/0216367 A1 | 11/2004 | Klein | |
| 2005/0138858 A1 | 6/2005 | Lyng | |
| 2006/0086038 A1 | 4/2006 | Mosher | |
| 2006/0283076 A1 | 12/2006 | Chambers et al. | |
| 2007/0044372 A1 | 3/2007 | Lang et al. | |
| 2007/0254907 A1 | 11/2007 | Bowles | |
| 2008/0052982 A1 | 3/2008 | Windsor | |
| 2008/0115406 A1 | 5/2008 | Duston et al. | |
| 2008/0269177 A1 | 10/2008 | Bessette | |
| 2008/0319029 A1 | 12/2008 | Richman et al. | |
| 2009/0145019 A1 | 6/2009 | Nolen et al. | |
| 2009/0145020 A1 | 6/2009 | McKnight | |
| 2009/0223115 A1 | 9/2009 | Lang et al. | |
| 2009/0313883 A1 | 12/2009 | Olson et al. | |
| 2010/0011655 A1 | 1/2010 | Frisch | |
| 2010/0212213 A1 | 8/2010 | Hope, III et al. | |
| 2011/0072712 A1 | 3/2011 | Black et al. | |
| 2011/0105333 A1 * | 5/2011 | Israels | A01N 25/10 |
| | | | 504/360 |
| 2011/0113674 A1 | 5/2011 | Levy | |
| 2011/0203159 A1 * | 8/2011 | McKnight | A01M 1/023 |
| | | | 43/123 |
| 2011/0289822 A1 | 12/2011 | Duehl et al. | |
| 2012/0012046 A1 | 1/2012 | Cain | |
| 2012/0110894 A1 | 5/2012 | Black | |
| 2012/0186137 A1 | 7/2012 | Schneidmiller et al. | |
| 2012/0192479 A1 * | 8/2012 | Schmitz | A01M 1/2094 |
| | | | 43/132.1 |
| 2012/0210628 A1 | 8/2012 | Park et al. | |
| 2012/0233907 A1 | 9/2012 | Pattison et al. | |
| 2012/0240451 A1 | 9/2012 | Ricks | |
| 2012/0285076 A1 * | 11/2012 | Banfield | A01M 1/026 |
| | | | 43/123 |
| 2012/0301532 A1 | 11/2012 | Carey et al. | |
| 2013/0031825 A1 | 2/2013 | Dass | |
| 2013/0067796 A1 | 3/2013 | Dong et al. | |
| 2013/0180161 A1 | 7/2013 | Vasudeva et al. | |
| 2013/0184153 A1 * | 7/2013 | Dieleman | A01N 43/90 |
| | | | 504/100 |
| 2013/0232849 A1 | 9/2013 | Schumacher | |
| 2013/0291427 A1 * | 11/2013 | Prohaska | A01M 1/023 |
| | | | 43/107 |
| 2013/0312313 A1 | 11/2013 | Lefkowitz et al. | |
| 2014/0020278 A1 | 1/2014 | Smith | |
| 2014/0020280 A1 | 1/2014 | Cullen | |
| 2014/0033597 A1 | 2/2014 | Vasudeva et al. | |
| 2014/0041284 A1 | 2/2014 | Nugent | |
| 2014/0187425 A1 * | 7/2014 | Allen | A01G 7/02 |
| | | | 504/116.1 |
| 2014/0290123 A1 | 10/2014 | Duff | |
| 2014/0311016 A1 * | 10/2014 | Wang | A01M 1/023 |
| | | | 43/123 |
| 2015/0007485 A1 | 1/2015 | Hortel et al. | |
| 2016/0316750 A1 * | 11/2016 | Gries | A01N 43/50 |
| 2017/0251655 A2 * | 9/2017 | Frutos | A01M 1/103 |

FOREIGN PATENT DOCUMENTS

| | | |
|---|---|---|
| EP | 0416255 | 3/1991 |
| KR | 20080036963 | 4/2008 |
| KR | 20100092641 | 8/2010 |
| KR | 20130122739 | 11/2013 |
| WO | 97/24034 A2 | 7/1997 |
| WO | WO2005070209 | 8/2005 |
| WO | 2008/030385 A2 | 3/2008 |
| WO | WO2009/047584 | 4/2009 |
| WO | WO2009/075839 | 6/2009 |
| WO | 2012/162703 A1 | 11/2012 |
| WO | WO2013115719 | 8/2013 |
| WO | 2014/028835 A2 | 2/2014 |
| WO | WO2015/089661 | 6/2015 |

OTHER PUBLICATIONS

Anderson, J.F. et al., A carbon dioxide, heat and chemical lure trap for the bedbug, Cimex lectularius, Medical and Veterinary Entomology, vol. 23, pp. 99-105 (2009).

Barcay, S.J. and Olson, J.F., From Detection through Protection: Solutions for Fighting Bed Bug Infestations, 13 pgs. (2010).

Bayer Environmental Science, Need to Know, Temprid® SC now labeled for Bed Bugs, vol. 7, No. 1, Feb. 18, 2010.

Cardinal Professional Products, ECO2FUME®, http://www.cardinalproducts.com/eco2fume.htm, 2 pages, printed Mar. 30, 2011.

Continental Carbonic, Use Dry Ice to Remove Bed Bugs, http://www.continentalcarbonic.com/dryice/remove-bed-bugs-dry-ice.php, 1 page, printed Sep. 20, 2010.

FMC Corporation, Best Management Practices, Bed Bugs, 2009 (3 pages).

Gries et al., Bed Bug Aggregation Pheromone Finaly Identified, Angewandte Chemie International Edition, Dec. 21, 2014, 5 pages.

Gries et al., Supporting Information Bed Bug Aggregation Pheromone Finaly Identified, Angewandte Chemie International Edition, Dec. 21, 2014, 24 pages.

(56) References Cited

OTHER PUBLICATIONS

International Search Report and Written Opinion for PCT/IB2012/052756 dated Jan. 29, 2013.
International Search Report and Written Opinion for PCT/US2015/017115 dated Jun. 1, 2015.
Luckow, Scientists Developing Pheromone-Laced Bed Bug Trap, Pest Control Technology, Jun. 2015, 2 pages.
MGK® Product Code 027911, Material Safety Data Sheet, BedlamTM Insecticide, Feb. 28, 2006 (2 pages).
National Center for Healthy Housing, What's Working for Bed Bug Control in Multifamily Housing: Reconciling best practices with research and the realities of implementation, undated (3 pages: cover page, table of contents, and p. 22).
Penn State University, Dept of Entomology, Entomological Notes, Bed Bugs, http://ento.psu.edu/extension/factsheets/bedbugs, printed Apr. 13, 2010 (4 pages).
Pest Management Professional, The Business of Bed Bugs, Michael F. Potter, Jan. 1, 2008 (8 pages).
Snell, Eric J., Smith, Todd, Sexton, Wally, Eclosion of Bed Bug (Cimex Lectularius) Eggs after Exposure to Various Compounds, Snell Scientifics LLC, Meansville, GA, submitted paper at the National Conference on Urban Entomology in Tulsa, OK, May 18-21, 2008 (1 page).
Stern Environmental Group, Bed Bug Control Services for Hotels, Motels, and Apartment Buildings; http://www.sternenvironmental.com/bedbugs/commercial.php, 3 pages, printed Sep. 20, 2010.
Supplementary European Search Report (EP 12 79 6003) dated Feb. 13, 2015 (8 pages).
TARR Status Report, http://tarr.uspto.gov/, Serial No. 77771410, Registration No. 3751703, mark:Bedlam Insecticide, printed Apr. 12, 2010 (2 pages).
Tvedten, Steve, The Bug Stops Here, http://www.getipm.com/thebestcontrol/bugstop/control_bed_bugs.htm, pages, printed Sep. 20, 2010.
www.bed-bug.net, Bed Bug Killer/How to Kill Bed Bugs/Bed Bug Information, printed Apr. 13, 2010 (1 page).
International Search Report and Written Opinion for International Application No. PCT/US2015/034715, dated Sep. 1, 2015, 15 pages.
Extended European Search Report for Application No. 15809461.5 dated Oct. 19, 2017.
Extended European Search Report for Aplication No. 15751451.4 dated Dec. 4, 2017.
Gangloff-Kaufmann, J.C. et al. (2006) Bed bugs in America: a pest management industry survey. Am. Entomol. 52: 105-106.
D.C. Robacker, "Attraction of both sexes of Mexican fruit fly, Anastrepha ludens, to a mixture of ammonia, methylamine, and putrescine," Journal of Chemical Ecology, vol. 19, No. 12, (1993).

\* cited by examiner

A = Bed Bug extract
B = 30 ppm each (TEA, Oleamide, Urea)
C = 30 ppm (TEA, Oleamide, Octanoic)
D = 100 ppm (TEA, Oleamide, Octanoic)

COMPOSITION FOR DETECTION AND TREATMENT OF BED BUGS

CROSS-REFERENCE TO RELATED APPLICATIONS

This application claims priority to Provisional Application Ser. No. 62/014,534 filed Jun. 19, 2014, and to Provisional Application Ser. No. 62/110,924 filed Feb. 2, 2015, each of which is incorporated herein by reference in its entirety.

FIELD

The present disclosure generally relates to the field of pest elimination including bed bugs. The present disclosure includes compositions and methods of product application to target and kill bed bugs.

BACKGROUND

Bed bugs are small parasitic insects that feed solely on the blood of animals, particularly humans. The common bed bug, *Cimex Lectularius*, is adapted to living with humans and prefers feeding on human blood. Bed bugs have lived with humans since ancient times, although many people living in the United States have never seen a bed bug. However, increase of international travel in recent decades has contributed to a resurgence of bed bugs in the United States. Many aspects of bed bugs make their eradication difficult once bed bugs have established a presence in a location.

Adult bed bugs are about ¼ inch or about 4-6 millimeters long, 3-5 millimeters wide, and reddish-brown with oval, flattened bodies. The immature nymphs are similar in appearance to the adults but smaller and lighter in color. Bed bugs do not fly, but they can move very quickly over surfaces. Female bed bugs lay their eggs in secluded areas and can deposit up to five eggs per day, and as many as 500 during a lifetime. The bed bug eggs are very small, about 1 mm in length. When first laid, the eggs are sticky, causing them to adhere to surfaces. The eggs hatch in about one to three weeks and go through five nymphal stages before reaching maturity in about 35-48 days.

Bed bug infestations begin by bed bugs crawling from place to place (e.g., from one room to another), or by a bed bug being carried into a new area. Bed bugs are able to cling to possessions and hide in small spaces so that they may easily be transported in a traveler's belongings or in furniture being moved. As a result, buildings where turnover of occupants is high, such as hotels or apartments, are especially vulnerable to bed bug infestations.

Bed bugs prefer to hide close to where they feed and will typically find a shelter or hiding place, such as a small crack or crevice in or around a bed or couch. Bed bugs are mainly active during the nighttime, making them hard to detect. Bed bugs easily find hiding places in beds, bed frames, furniture, along baseboards, in carpeting, behind loose wall paper, and countless other places. Once established in a location, bed bugs tend to aggregate but do not build nests like some other insects.

Infestations are not likely to be eliminated by leaving a location unoccupied as bed bugs can survive long periods of time without feeding. Adult bed bugs can persist months without feeding, and in certain conditions even up to a year or more. Nymphs can survive weeks or months without feeding.

Bed bugs obtain their sustenance by drawing blood from a mammal through an elongated proboscis (or beak). They may feed on a human for 3 to 10 minutes although the person is not likely to feel the bite. After the bite, the victim may experience an itchy welt or swelling in the area of the bite. However, some people do not have any reaction or only a very minor reaction to a bed bug bite. Bed bug bites have symptoms that are similar to other insect bites, such as mosquitoes and ticks. It is not possible to determine whether the bite is from a bed bug or another type of insect without actually observing the bed bug or detecting nearby products of an infestation. As a result, bed bug infestations may go long periods without being detected.

Bed bugs are difficult to completely eradicate because of their tendency to hide, their ability to survive long times without food, and the small size of the eggs. In order to detect, trap, and/or eradicate bed bugs, it would be beneficial to provide for a composition and method to attract bed bugs to a trap or to a location where an insecticide or pesticide is present.

SUMMARY

The present disclosure provides for a composition and method for attracting bed bugs to a trap or to a location where an insecticide or pesticide is present, or to a trap or a location where a bed bug infestation can be detected.

The present disclosure provides for a composition for attracting bed bugs comprising one or more of methyl diethanolamine (MDEA), monoethanolamine (MEA), diethanolamine (DEA), triethanolamine (TEA), and dimethyl trisulfide (DMTS); a carrier; and optionally one or more amides selected from oleamide, octanamide, nonanamide, and laurylamide; urea, biuret, or triuret; and one or more aliphatic fatty acids. The composition may also comprise trimethylamine (TMA), histamine, or alkanolamines. The present disclosure further provides for a method for treating an article by applying the composition to the article, wherein the article comprises a device for trapping or detecting bed bugs or a device for treating a bed bug infestation. The present disclosure also provides for a method of treating an area suspected of bed bug infestation or at risk of infestation by bed bugs.

DETAILED DESCRIPTION

Figure 1:
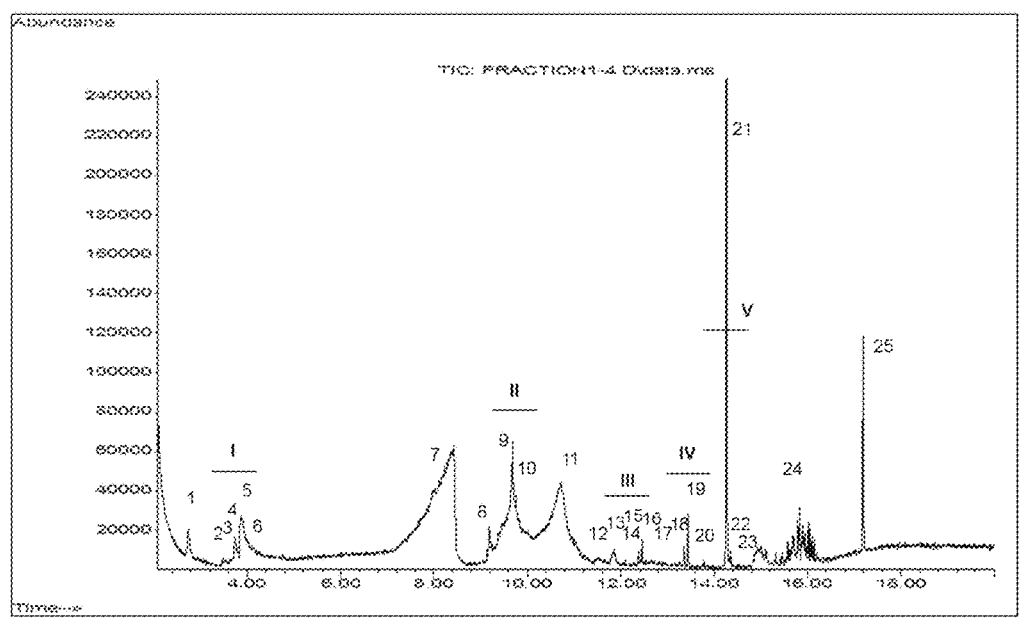
FIG. 1 shows a total ion chromatogram of a pheromone composition.

Pest removal services are often called upon to eradicate bed bugs in infested locations such as homes, hotels, offices, or theaters. Because of the characteristics of bed bugs, particularly the tendency to hide, nocturnal activity, and resistance to some treatments, eliminating the infestation may take several visits and consecutive treatments. The composition and method of this disclosure provide for an improved way to eradicate bed bugs, as the bed bugs can be attracted from hiding in order to be detected or trapped, and attracted into a treatment area, making the treatment more effective. The composition and method can also be used to treat areas proactively before infestation occurs.

Like many animals, bed bugs are capable of secreting pheromones. Pheromones are chemicals that send signals to other members of the same species and can change their behavior or physiology accordingly. For example, pheromones can signal alarm, food, territory, or breeding readiness, among other things. Some pheromones, such as arrestment and/or aggregation pheromones, can attract other members of the species to the location where the pheromone is released or deposited.

Pheromones secreted by animals (e.g., bed bugs) may comprise a complicated cocktail of chemical compounds. According to an embodiment, components of bed bug excretions were identified and tested to find the suitable attractants and combinations of attractants, which can then be used in conjunction with a treatment regimen to improve the efficacy of the treatment. In an embodiment, the selected attractant can be provided in a pheromone composition that may comprise other pheromone components and/or other ingredients. In an exemplary embodiment, the pheromone composition can be applied in combination with an insecticide. In another exemplary embodiment, the pheromone component can be used conjunctively with a bed bug trap. The pheromone composition may also be utilized in detection of bed bugs when an infestation is suspected or there is a risk of infestation and early detection and control is warranted.

According to an embodiment, the composition comprises one or more pheromone components found in pheromones naturally secreted by bed bugs. The pheromone components may be of natural origin (e.g., isolated from an extract including pheromones) or synthetic. The pheromone components may include one or more of aliphatic saturated or unsaturated fatty acids, urea or urea-related components, alkanolamines, alkyl trisulfides, alkyl disulfides, and amides of aliphatic fatty acids. In an exemplary embodiment, the composition comprises one or more of octanoic acid, triethanolamine, methyl diethanolamine (MDEA), dimethyl trisulfide (DMTS), urea, and oleamide. In preferred embodiments, less volatile pheromone components are chosen over more volatile ones, as the more volatile components may have an unpleasant odor or dissipate too rapidly. Without wishing to be bound by theory, it is hypothesized that some pheromone components may provide a synergistic effect. Accordingly, in some embodiments, the composition comprises pheromone components selected to provide a synergistic effect. The pheromone components may be isolated from a natural source or may be synthetic. The composition may include a combination of synthetic and natural origin pheromone components.

The term "about" is used here in conjunction with numeric values to include normal variations in measurements as expected by persons skilled in the art, and is understood have the same meaning as "approximately" and to cover a typical margin of error, such as ±5% of the stated value.

The transitional phrase "consisting essentially of" as used in the composition claims and the disclosure here, limits the scope of the claim to the specified materials including only minor impurities or inactive agents that a person of ordinary skill in the relevant art would ordinarily associate with the listed components.

The term "active ingredients" is used here to refer to the pheromone components in the composition, as well as any pesticidal or insecticidal components, if included. In typical embodiments, the composition is used by applying the composition to a surface. When the composition is applied to a surface, the carrier may evaporate, leaving relatively pure active ingredients on the surface. The concentrations discussed below, unless otherwise stated, refer to a use composition that includes a carrier and that can be applied to a surface as described. However, the composition can be provided as a concentrate, and can be applied to a surface in various ways, including spraying, aerosolized spraying, misting, fogging, dispersing, wiping on with a cloth, or by applying as drops from a dropper. The composition can be applied to the surface in amounts ranging from about $5.0 \times 10^{-6}$ μg/cm$^2$ to about $1.5 \times 10^{-2}$ μg/cm$^2$, or from about $1 \times 10^{-5}$ μg/cm$^2$ to about $2.5 \times 10^{-3}$ μg/cm$^2$, or from about $2 \times 10^{-5}$ μg/cm$^2$ to about $2 \times 10^{-3}$ μg/cm$^2$, or from about $3 \times 10^{-5}$ μg/cm$^2$ to about $1 \times 10^{-3}$ μg/cm$^2$, or from about $5 \times 10^{-5}$ μg/cm$^2$ to about $1 \times 10^{-3}$ μg/cm$^2$ of active ingredients.

According to an embodiment, the composition comprises one or more aliphatic saturated or unsaturated fatty acids or their salts. The composition may comprise, for example, about 0.1-300 ppm (i.e, about 0.00001-0.03 wt-%), about 0.3-200 ppm, about 0.5-100 ppm, about 0.7-50 ppm, about 0.8-40, or about 1-30 ppm aliphatic fatty acid. The aliphatic fatty acid may comprise 6-20 carbon atoms, or 6-14 carbon atoms, or 8-12 carbon atoms. In an embodiment the aliphatic acid is octanoic acid, a saturated C8 fatty acid also known as caprylic acid. In an exemplary embodiment, the composition includes about 0.5-300 ppm octanoic acid. In an alternative embodiment the aliphatic acid is hexanoic acid (C6), or decanoic acid (C10). In another embodiment the aliphatic acid is an unsaturated fatty acid, such as oleic acid (C18:1) or ricinoleic acid (C18:1 hydroxyoctadecenoic acid). The aliphatic acid may also be a branched chain acid, such as 2-methyl propanoic acid.

The composition may comprise dicarboxylic acids. Examples of dicarboxylic acids include hexanedioic acid, heptanedioic acid, octanedioic acid and nonanedioic acid. The composition may also comprise one or more aromatic carboxylic acids. Examples of aromatic carboxylic acids are benzoic acid and phenolic acids. The composition may further comprise esters of aliphatic fatty acids, such as C1-C4 ester of C6-C20 fatty acid. An example of an ester of an aliphatic fatty acid is propyl ester of hexadecanoic acid.

According to an embodiment the composition comprises urea. For example, the composition may comprise about 0.1-300 ppm, about 0.3-200 ppm, about 0.5-100 ppm, about 0.7-50 ppm, about 0.8-40, or about 1-30 ppm urea. In an alternative embodiment the composition comprises a urea-derivative, such as biuret ($H_2NC(O)NHC(O)NH_2$) or triuret ($H_2NC(O)NHC(O)NHC(O)NH_2$).

In an embodiment the composition comprises one or more amines, such as alkylamines or alkanolamines (i.e., amine alcohols), including primary amines, secondary amines, and tertiary amines. In general, the alkyl and alkanol chains of the amines may be between 1-5 carbons in length. Examples of suitable amines include trimethylamine (TMA), isopropylamine, trimethanolamine, monoethanolamine (MEA), diethanolamine (DEA), triethanolamine (TEA), methyl diethanolamine (MDEA), bicine (2-(bis(2-hydroxyethyl)amino)acetic acid), and histamine. The composition may comprise about 0.1-300 ppm, about 0.3-200 ppm, about 0.5-100 ppm, about 0.7-50 ppm, about 0.8-40, or about 1-30 ppm alkanolamine. In an exemplary embodiment, the composition includes about 0.5-300 ppm TEA. In another exemplary embodiment, the composition includes about 0.5-300 ppm MDEA.

According to an embodiment, the composition comprises one or more amides of aliphatic fatty acids. The composition may comprise, for example, about 0.1-300 ppm, about 0.3-200 ppm, about 0.5-100 ppm, about 0.7-50 ppm, about 0.8-40, or about 1-30 ppm fatty acid amide. The fatty acid may be saturated or unsaturated and may include 6-18 carbon atoms. Examples of amides of aliphatic fatty acids include oleamide (oleic acid amide, C18:1), octanamide (octanoic acid amide, C8), nonanamide (nonanoic acid amide, C9), and laurylamide (lauric acid amide, C16). In an exemplary embodiment the composition comprises 0.5-300 ppm oleamide.

In some embodiments, the composition comprises dimethyl trisulfide (DMTS), dimethyl disulfide (DMDS), diethyl trisulfide (DETS), or methylmethanethiosulfonate (MMTS). The composition may comprise between about 0.4 to 400 ppm, about 0.5 to 100 ppm, about 0.6 to 50 ppm, about 0.7 to 40 ppm, about 0.8 to 30 ppm, about 0.9 to 20 ppm, or about 1 to 10 ppm of DMTS, DMDS, DETS, or MMTS. In certain embodiments, the composition comprises DMTS.

In an exemplary embodiment, the composition comprises at least about 0.5 ppm, 0.75 ppm, or 1 ppm of active ingredients (pheromone components). For example, the composition may comprise between about 0.5-100 ppm, or about 0.6-50 ppm, or about 0.7-40 ppm, or about 0.8-30 ppm, or about 0.9-20 ppm, or about 1-10 ppm of pheromone components. In one embodiment, the composition comprises one or more of MDEA, TEA, DMTS, oleamide, and urea in a total concentration of about 0.5-30 ppm. In one exemplary embodiment, the composition comprises between about 0.1-10 ppm each of MDEA, DMTS, and optionally TEA, oleamide, or octanoic acid. In another exemplary embodiment, the composition comprises about 0.5-50 ppm each of TEA, oleamide, and urea. In another exemplary embodiment, the composition comprises between about 10-50 ppm each of TEA, oleamide and octanoic acid.

In one embodiment, the composition comprises at least one of MDEA, DMTS, or TEA. In a preferred embodiment, the composition comprises at least two of MDEA, DMTS, and TEA.

The composition may further comprise additional components, such as carriers, surfactants, emulsifiers, drying agents, film forming agents, and combinations thereof. The types and concentrations of additional components can be selected based on the intended formulation and use of the composition, such as use of a gel, paste, liquid, powder, granule, pellet, etc., by spraying, misting, fogging, dispersing, or wiping. In some embodiments, the composition consists essentially of a pheromone component and functional agents selected from carriers, surfactants, emulsifiers, drying agents, film forming agents, and combinations thereof. In other embodiments, the composition additionally includes an insecticide.

The carrier and its concentration may be selected based on the intended use of the composition. For example, a composition intended to be used as a spray may comprise a liquid carrier, such as water or a water based solution, e.g., an aqueous solvent, such as an alcohol (e.g., methanol, ethanol, propanol, butanol, etc., and mixtures thereof) or polyol (e.g., glycerol, ethylene glycol, propylene glycol, diethylene glycol, etc., and mixtures thereof). In an exemplary embodiment the composition is formulated as a use solution and comprises about 85-99.9 wt-% liquid carrier, or about 90-99 wt-% liquid carrier, or about 92-98 wt-% liquid carrier. In another exemplary embodiment the composition is a concentrate and comprises up to about 50 wt-% liquid carrier.

The composition may have a pH of about 3 to about 12, about 4 to about 10, or about 5 to about 9. The pH of the composition may be adjusted with a suitable pH adjusting agent (e.g., an acid, base, or a buffer) if necessary.

A composition intended to be used as a dust or powder may comprise a solid carrier, such as talc, clay, chalk, volcanic ash, or other inert ingredient. A composition intended to be used as a solid bait may comprise feed, meal, grain, flour, or other similar ingredient.

Surfactants and emulsifiers can be used to aid solubility of the composition or of the components of the composition, and to improve homogeneity of the composition. Surfactants may also be used to lower surface tension and to aid the application of the composition, e.g., by spraying. Suitable surfactants include, for example non-ionic, cationic, anionic, zwitterionic (amphoteric), or semi-polar non-ionic surfactants and combinations thereof. Exemplary emulsifiers include fatty carboxylic acids, fatty carboxylic acid salts, and esters of fatty carboxylic acids, such as polyglyceryl oleate, polyglyceryl stearate, or lecithin. The surfactants and emulsifiers can be selected based on the intended use of the composition. For example, a surfactant and/or emulsifier can be incorporated into the composition to improve solubility of active ingredients, to form an emulsion, to improve wettability, or other similar purposes. The composition may comprise about 0-20 wt-% surfactants, or about 0.5-15 wt-% surfactants. In an exemplary embodiment the composition comprises about 1-10 wt-% sodium lauryl sulfate.

Drying agents can be used to aid drying properties of the composition, e.g., when the composition is used as a spray. Drying agents include components that evaporate rapidly, such as solvents. Suitable drying agents include, for example, alcohols (e.g., methanol, ethanol, propanol, butanol, etc., and mixtures thereof). In an exemplary embodiment the composition comprises about 0-50 wt-% drying agents, or about 2-25 wt-% drying agents. In a solid composition (e.g., a powder or a bait), a solid drying agent can be used. Drying agents suitable for solid compositions include components with desiccating properties, such as activated alumina, aerogel, benzophenone, bentonite clay, calcium chloride, calcium sulfates, cobalt(II) chloride, copper(II) sulfate, lithium chloride, lithium bromide, magnesium sulfate, magnesium perchlorate, molecular sieves, potassium carbonate, silica gel, sodium chlorate, sodium chloride, sodium hydroxide sodium sulfate, and sucrose.

The compositions may also optionally include humectants such as glycerol/glycerine, glycol, or other suitable components to slow evaporation and maintain wetness of the composition after application. When a humectant is included in the composition, the humectant may constitute about 0.5-10 wt-% of the compositions.

The composition can optionally include a film forming agent. Preferred film forming agents have a glass transition temperature (Tg) greater than 20° C. and are water-resistant. Exemplary film forming agents include gums such as tragacanth, karaya, acacia, carrageenan, locust bean, guar, pectin, xanthan gum, diatomaceous earth, and silica gel; cellulosic derivatives such as alkyl and hydroxyalkylcelluloses, specifically methylcellulose, hydroxyethylmethylcellulose, hydroxypropylmethylcellulose, hydroxybutylmethylcellulose, hydroxyethylcellulose, ethylhydroxyethylcellulose, hydroxypropylcellulose, and carboxymethylcellulose; gelatin; polyvinyl alcohol; and synthetic water-soluble polymers such as polyvinylpyrrolidone, polyvinylmethylether, polyacrylic acid, polymethacrylic acid, polyacrylamide, polyethylene oxide, polypropylene oxide, and polyethyleneimine.

The composition may optionally be formulated as a micro encapsulated formulation or a formulation that provides a delayed release. Micro encapsulation may be achieved with one or more of the film forming agents or pre-formed beads (e.g., selective release polymer beads).

The composition may optionally be formulated with an insecticide or pesticide, or be used in combination with an insecticide. Suitable pesticides include, for example, 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluoron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram (XDE-175), spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos, and combinations thereof.

The pesticides may also include surfactant pesticides such as sodium lauryl sulfate, alcohol ethoxylates, quaternary ammonium compounds, fatty acids, fatty acid soaps, dioctylsulfosuccinate, and mixtures thereof. The compositions may also include an additional insecticide, for example, a reduced risk pesticide as classified by the Environmental Protection Agency (EPA). Reduced risk pesticides include pesticides with characteristics such as very low toxicity to humans and non-target organisms, including fish and birds, low risk of ground water contamination or runoff, and low potential for pesticide resistance. Exemplary active ingredients for reduced risk pesticides include castor oil, cedar oil, cinnamon, cinnamon oil, citric acid, citronella, citronella oil, cloves, clove oil, corn gluten meal, corn oil, cottonseed oil, dried blood, eugenol, garlic, garlic oil, geraniol, geranium oil, lauryl sulfate, lemon grass oil, linseed oil, malic acid, mint, mint oil, peppermint, peppermint oil, 2-phenethyl propionate (2-phenyethyl propionate), potassium sorbate, potassium oleate, putrescent whole egg solids, rosemary, rosemary oil, sesame, sesame oil, sodium chloride, soybean oil, thyme, thyme oil, white pepper, and zinc metal strips. In some embodiments, the composition can be used in conjunction with a commercially available pesticide, such as Finito®(available from Ecolab Inc. in St. Paul, Minn.), Tempo® (available from Bayer Professional Care in Whippany, N.J.), Temprid® (available from Bayer Professional Care), or Phantom® (available from BASF in Florham Park, N.J.).

The composition may also include other components or additives, such as fragrances, dyes, rheology modifiers, thickeners, solvents, and wetting agents.

The composition can be a concentrate or a ready-to-use composition. A concentrate refers to a composition that is diluted to form the ready-to-use composition. A ready-to-use composition refers to the composition that is applied to a target. A concentrate composition can be diluted before use, for example in a ratio of 1:2, 1:3, 1:4, 1:5, 1:10, 1:20, 1:50, 1:99, or any other suitable ratio that results in an effective amount of active ingredients (pheromone components and/or pesticides) in the diluted solution.

The disclosed compositions can be used on a variety of surfaces and in a variety of locations. For example, the disclosed compositions can be used to treat surfaces, textiles, furniture, and structures, including mattresses, box springs, beds, bed frames, cushions, chairs, sofas, seats, and other upholstered furniture, booths; textiles, carpets, rugs, clothing, and toys; closets, dressers, cabinets, drawers, tables, etc.; personal items, books, electronics, picture frames, etc.; cracks and crevasses between floor boards, behind base boards, head boards, furniture, and wall paper. The composition may be used, for example, in residential and lodging structures (e.g., homes, multi-family residences, dormitories, hotels, motels, hostels, etc.), food service facilities (e.g., restaurants, cafes, cafeterias, mess halls, etc.), offices, government buildings, military facilities, transportation vehicles (e.g., buses, trains, airplanes, cars, etc.), vessels (e.g., boats, submarines, cruise liners, ships, ferries, etc.), homeless shelters, entertainment facilities (e.g., theaters, movie theaters, casinos, etc.), or in patient rooms and common areas in healthcare and long-term care facilities. The compositions can be used to treat the entrances to buildings, around drive through windows, road surfaces near drive through windows, or the concrete or dumpster containers outside of buildings. In general, the composition may be used in any location occupied by people, or where belongings could be placed and bed bugs may have an opportunity to transfer from a person or his/her belongings to the surroundings.

In some embodiments, the compositions can be used as part of a treatment or program to prevent, control, or eliminate pests. The composition can be used as an attractant that is used to attract insects (e.g., bed bugs) to a trap, or used to attract insects to an area that is treated with an insecticide. Alternatively, the composition can be used to attract insects to the composition itself when the composition is formulated to kill the insects on contact, e.g., when the composition includes a pesticide or insecticide.

In some embodiments, the composition is used to treat an area that is at risk for being contaminated with bed bugs proactively before an actual bed-bug infestation occurs. For example, the composition can be used to treat a hotel room, a rental home, a care facility, or a transportation vehicle prior to contamination. If bed bugs are later introduced to the area (e.g., brought in in the belongings of a traveler or occupant), the bed bugs will be attracted to the composition, which may prevent the bed bugs from becoming established in the area. It has surprisingly been found that using the composition together with an insecticide not only kills bed bugs, but also lowers the number of eggs laid by any surviving bed bugs, thus making it less likely that the bed bugs will be able to establish a colony in a new location. The insecticide used with or in the composition can be selected so that the treatment is effective for a number of days after it is applied. For example, the treatment can be effective for at least 1 week, 2 weeks, 3 weeks, 4 weeks, or 8 weeks after application. In some embodiments, the composition can be effective for several months, e.g., 3 months, 4 months, 5 months, or 6 months.

In an embodiment, the composition is applied to a trap or other treatment device that can be used to detect, capture, or kill bed bugs. An exemplary bed bug monitoring device is described in U.S. Pat. No. 7,591,099. An exemplary trap is described in U.S. Provisional patent application Ser. No. 14/628,433. An exemplary device for treating articles for bed bugs is described in U.S. patent application Ser. No. 13/421,409. The composition can be applied by spraying, painting, immersing, smearing, dusting, fumigating, or by any other suitable method. The composition can be applied to the surface of the trap or device, into or next to a bait, into a portion of the trap or device, or impregnated into the material of the trap or device.

According to an embodiment, the composition is applied to a bed bug detection device (e.g., a trap) by spraying or painting. The device is used to detect and/or capture bed bugs by placing the device in an area of a bed bug infestation or a suspected bed bug infestation. The composition acts to attract bed bugs onto or into the device, facilitating detection and/or capture of bed bugs and subsequent treatment of the area. The trap may include an immobilizing element, such as an adhesive, an electric trap, a chemical immobilizer (e.g., an insecticide), or other means for immobilizing the bed bugs.

Figure 9A:
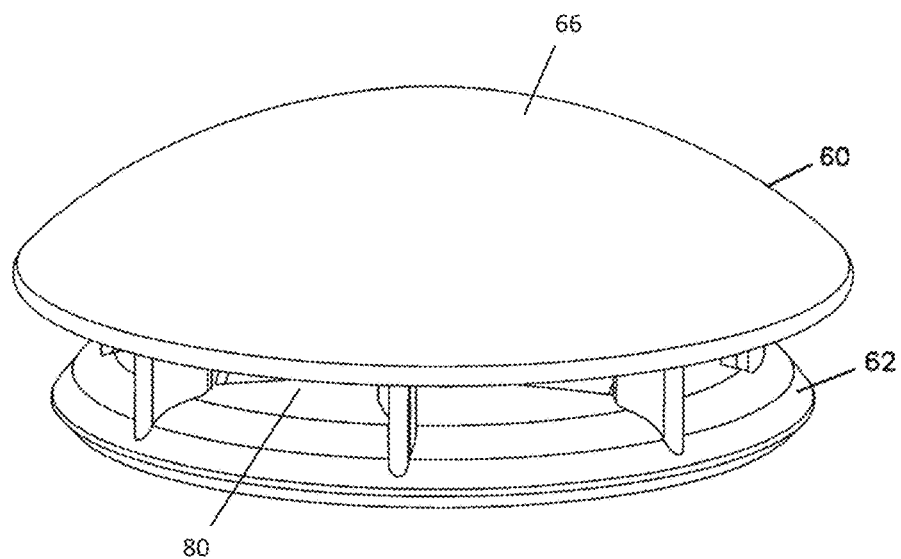
FIGS. 9A and 9B are schematic views of a trap comprising a pheromone composition according to an embodiment.
Figure 9B:
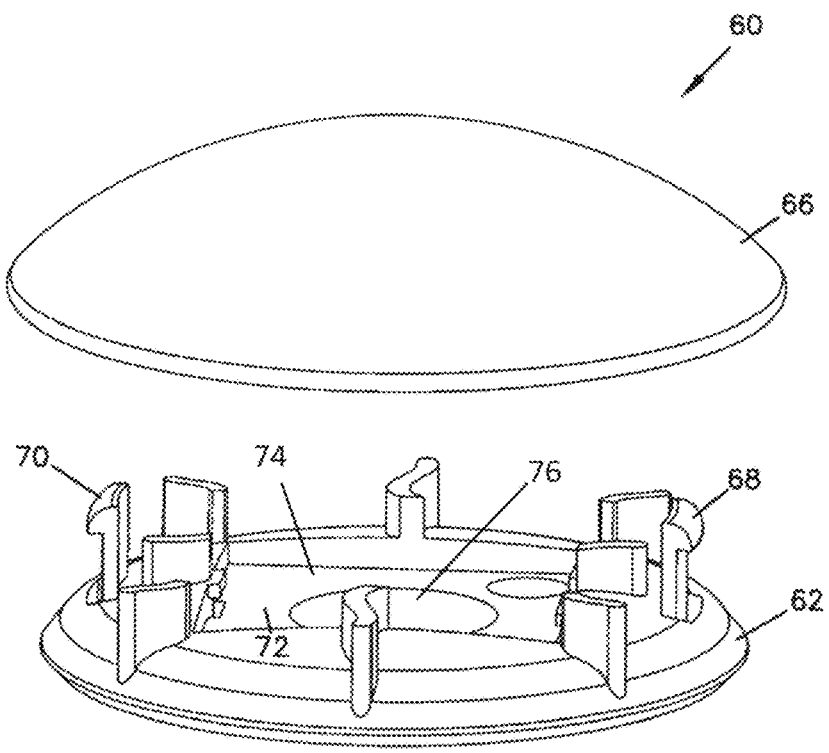

An exemplary embodiment of the composition incorporated in a trap 60 is schematically shown in FIGS. 9A and 9B. The trap 60 may include a base 62 and a removable cover 66. The base may include a receiving area 72 that can be used to receive an adhesive element 74 (e.g., a glue board) or insecticide and an attractant element 76 onto which the composition can be applied. The composition attracts bed bugs into the trap 60 through the gap 80 between the base 62 and the cover 66.

Figure 10:
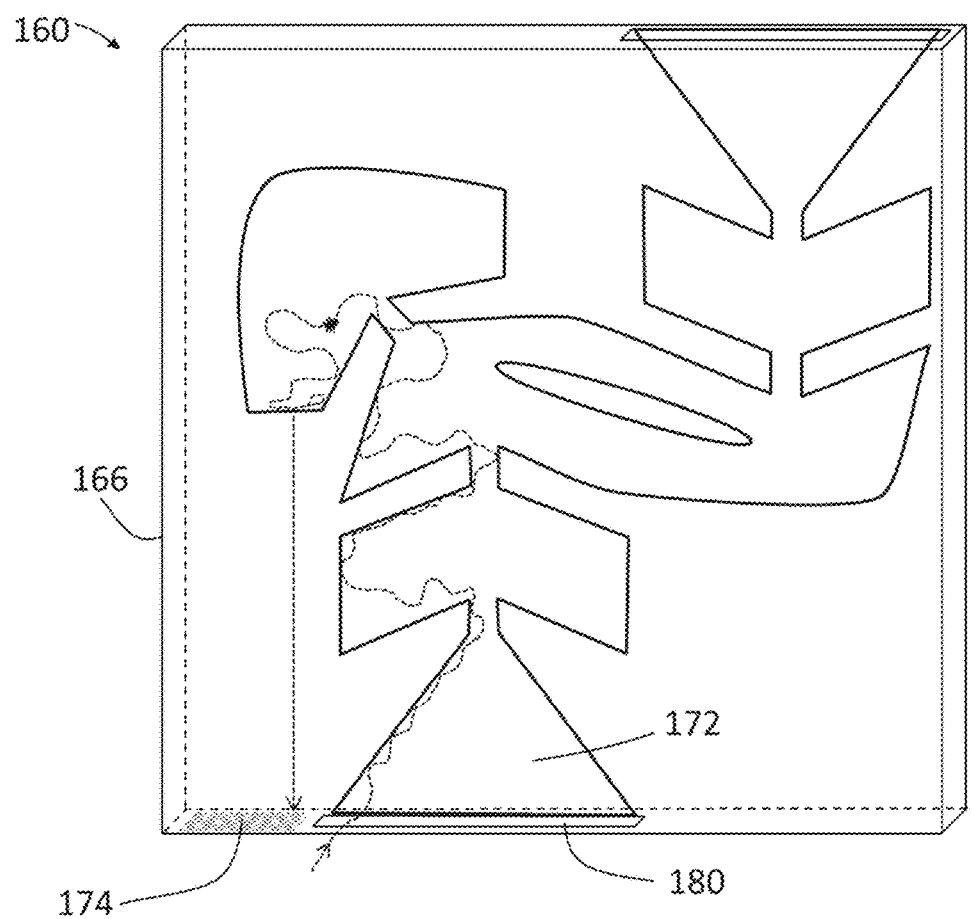
FIG. 10 is a schematic view of a trap comprising a pheromone composition according to an embodiment.

An alternative embodiment of the composition incorporated in a trap 160 is shown in FIG. 10. The trap 160 includes a housing 166 with a receiving area 172 positioned inside the housing. The receiving area 172 has a rough surface texture that is preferred by bed bugs. The housing 166 includes one or more openings 180 through which insects can enter the trap 160. The trap can include an adhesive element 174 or insecticide that immobilizes the insects.

In another embodiment, the composition is applied to a device (e.g., a thermal enclosure) for treating articles (e.g., furniture or clothing) for bed bugs. The composition acts to attract bed bugs from the article being treated so that the bed bugs can be more effectively exposed to the treatment (e.g., heat or pesticide treatment).

The composition can be used in a variety of forms such as a gel, foam, aerosol, thin liquid, thickened liquid, paste, powder, solid, pellet, granules, microcapsules, lotion, or cream. The composition is preferably a spray, powder, pellet, or granule. The compositions may be applied to the surface in a variety of ways such as spraying, misting, fogging, dispersing, wiping on with a cloth, or by applying as drops from a dropper.

EXAMPLES

Bed bug pheromones were extracted from bed bug stained papers by soaking the stained papers in methanol.

Bed bugs were obtained from stock cultures of the ECL-05 field strain of *Cimex lectularius* (Olson et al., *Off-host Aggregation Behavior and Sensory Basis of Arrestment by Cimex lectularius*, J. Insect Physiology 55 (2009) 580-587). Colonies were maintained under standard conditions of 25° C. and 14:10 (light:dark) in 473 mL (16 oz) glass jars with folded pieces of filter papers (9.0 cm diameter, available from Fisher Scientific) provided for harborage and egg deposition. Colony jars were covered with a fine mesh fabric (Precision Woven Nylon Mesh 193×193, available from McMaster Can, Chicago, Ill., USA) with a pore size of 78 µm for ventilation and containment. Colonies were fed weekly using an artificial feeding system (adapted from a system described in Montes et al., 2002) that included a stretched Parafilm® membrane (available from Bemis Flexible Packaging, Neenah, Wis.) to feed through soon-to-expire stocks of human blood obtained from the American Red Cross (St. Paul, Minn.).

Example 1

Pheromone composition from bed bug excretions was analyzed by GC/MS (gas chromatography/mass spectroscopy). To obtain the sample, approximately 10 fecal-stained filter papers that had been used for colony maintenance as described above were cut into 1 cm strips lengthwise and soaked in 80 mL of methanol overnight to extract the bed bug aggregation pheromones. The methanol was decanted off into a 100 mL glass jar and evaporated under a gentle stream of nitrogen. After decanting, another 80 mL of methanol was added to the filter paper strips and this process was repeated three more times. Approximately 90 mg of dried material was reconstituted in 4 mL of $H_2O$ and filtered through a Millex-HV, 0.45 µm PVDF filter disk (available from Millipore Corp. in Bedford, Mass.) to remove any undissolved material. The filtrate was then loaded onto a C18 Sep-Pak column (available from Waters, Inc. in Milford, Mass.) and was eluted using 2 mL aliquots of methanol-water solutions of increasing polarity, starting with 100% water and ending with 100% methanol. The aliquots were further analyzed by GS/MS.

A total ion chromatogram (TIC) of the first aliquot eluted with 100% water is shown in FIG. 1. The peaks identified in the TIC are shown in TABLE 1.

TABLE 1

| Group | Peak No. | Component | Concentration (ppm) |
|---|---|---|---|
| I | 1 | Dimethyl trisulfide (DMTS) | 0.95 |
| I | 2 | Dimethylpropanamide | 0.2 |
| I | 3 | amyl-butyl amine | 0.05 |
| I | 4 | Methylmethanethiosulfonate | 0.63 |
| I | 5 | methyldiethanol amine (MDEA) | 3.75 |
| I | 6 | ethanediamide | 0.09 |
|  | 7 | urea | 41.46 |
| II | 8 | bicine | 0.93 |
| II | 9 | Triethanolamine (TEA) | 17.01 |
| II | 10 | N,N-bis(2-hydroxyethyl)formamide | 0.22 |
| II | 11 | column bleed | N/A |
| III | 12 | dimethylpyridinone | 0.60 |
| III | 13 | column bleed | N/A |
| III | 14 | octamide | 0.03 |
| III | 15 | palmitic acid | 0.15 |
| III | 16 | nonamide | 0.27 |
| IV | 17 | 4-methyl pentanamide | 0.38 |
| IV | 18 | 7-nonenamide | 0.26 |
| IV | 19 | lauramide | 0.57 |
| IV | 20 | branched amide | 0.03 |
| V | 21 | oleamide | 6.91 |
| V | 22 | stearamide | 0.10 |
|  | 23 | phosphorous species | N/A |
|  | 24 | phthalates | N/A |
|  | 25 | lanol | 2.5 |

Example 2

Bed bug excretions were collected and separated into groups of components using liquid chromatography. The effectiveness of the groups of components to attract bed bugs was tested as described in Example 4. The most effective groups were further analyzed using GC/MS.

The GC/MS conditions were as follows:
Column: ZB-5MS, 30 m, 0.25 mm, 0.25 μm film
Initial Temp: 60° C. (2 min hold)
Final Temp: 320° C. (10 min hold)
Ramp Rate: 20° C./min
Injection: 2 μL
Injector: PTV splitless
Scan: 50-750 amu Samples were analyzed without dilution, both as-is and derivatized with BSTFA (bis trimethylsilyl trifluoracetamide).

Figure 2A:
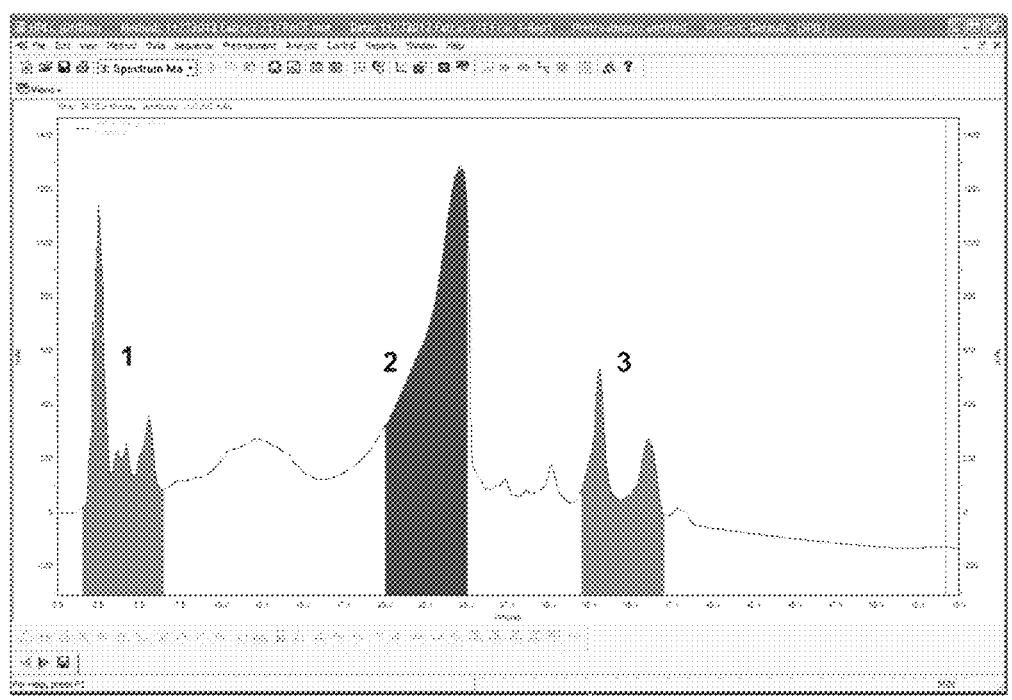
FIG. 2A shows a chromatogram of a pheromone composition.
Figure 2B:
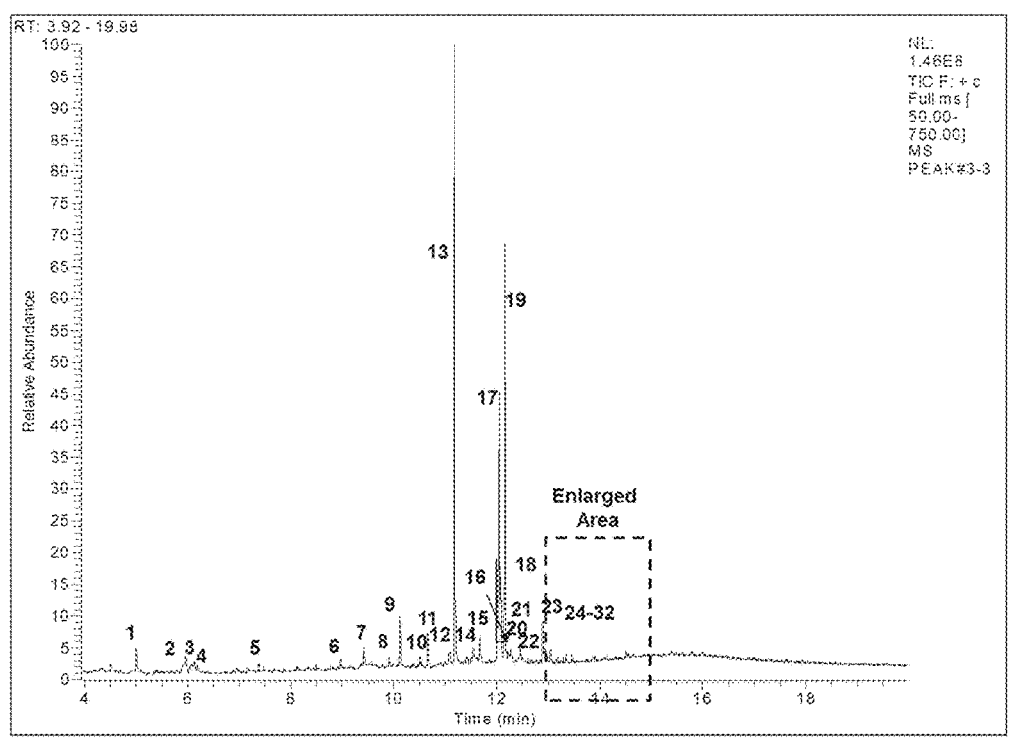
FIG. 2B shows a total ion chromatogram of a portion of the pheromone composition of FIG. 2A.

Results from the initial separation are shown in FIG. 2A, where groups of components are designated as 1-3. A further separation of group 3 is shown in FIGS. 2B (sample injected as-is), 2C (enlarged area as noted in FIG. 2B), 2D (derivatized sample, 5-9 minutes), and 2E (derivatized sample, 8.5-14 minutes). A list of identified components is shown in TABLE 2.

hypothesized that the extract could get bed bugs to remain longer on the surface.

Test Arena Set-up: the assays were performed using 20 cm diameter circular arenas previously described by Olson et al. (2009). Each arena contained two 25 mm glass microfiber filter disks (Whatman® Grade GF/A, available from GE Healthcare in Piscataway, N.J.) attached to the arena about 10 cm apart. In each test run, one disk was treated and the other one untreated. The treated disk was treated either with an insecticide or insecticide+extract.

Figure 3A:
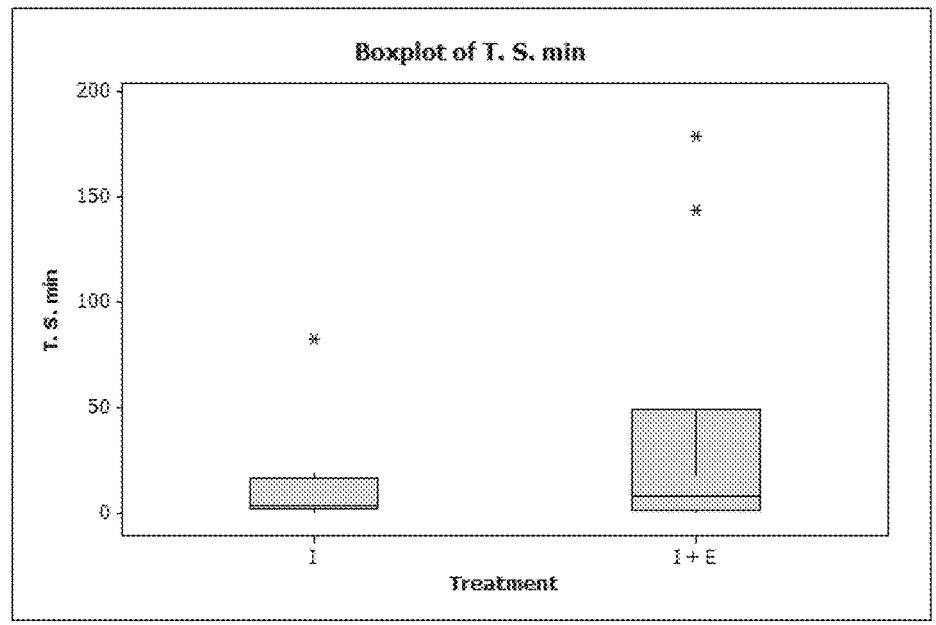
FIG. 3A is a box plot graph showing results of testing the efficacy of a pheromone composition according to an embodiment.

To measure time spent on the treated surface, one bed bug was introduced into the arena and its movement was recorded over a 4 h time period. The total amount of time spent (T.S. min) on/under the treated disk was calculated, and time spent on/under the insecticide treated disk was compared to time spent on/under the disk treated with insecticide and extract. The results are shown in FIG. 3A.

To measure the impact of the extract on the efficacy of the insecticide, 10 bed bugs were introduced into the arena and % mortality was recorded over six days for insecticide alone and for insecticide and extract combined. The results are

TABLE 2

Figure 2C:
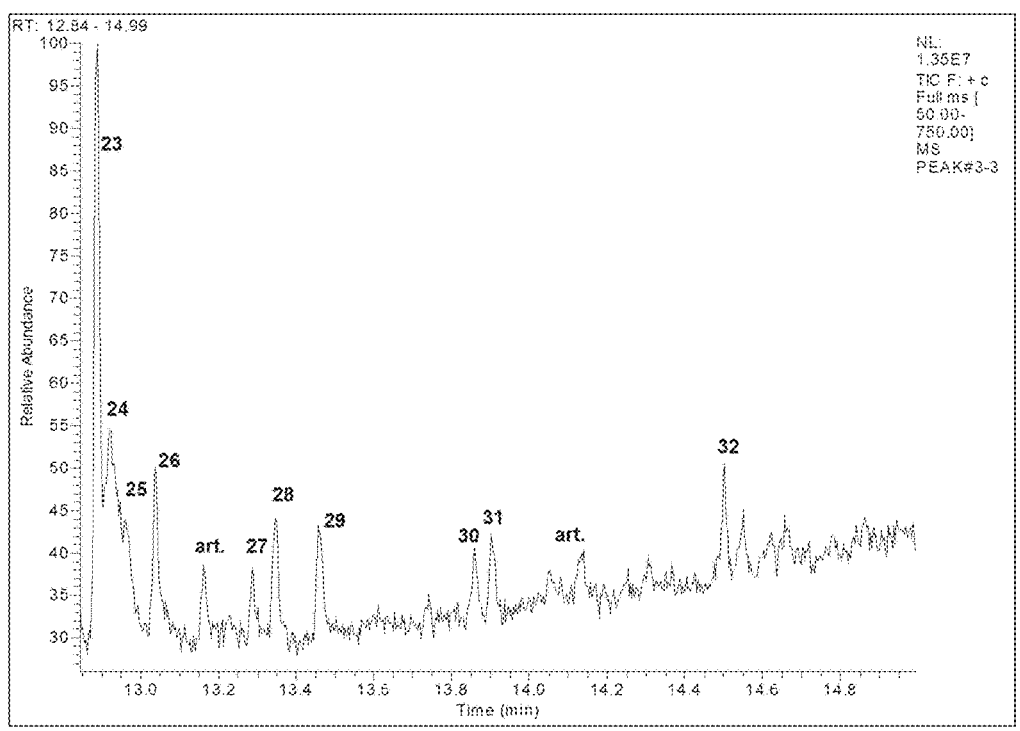
FIG. 2C shows an enlarged view of a part of the total ion chromatogram of FIG. 2B.
Figure 2D:
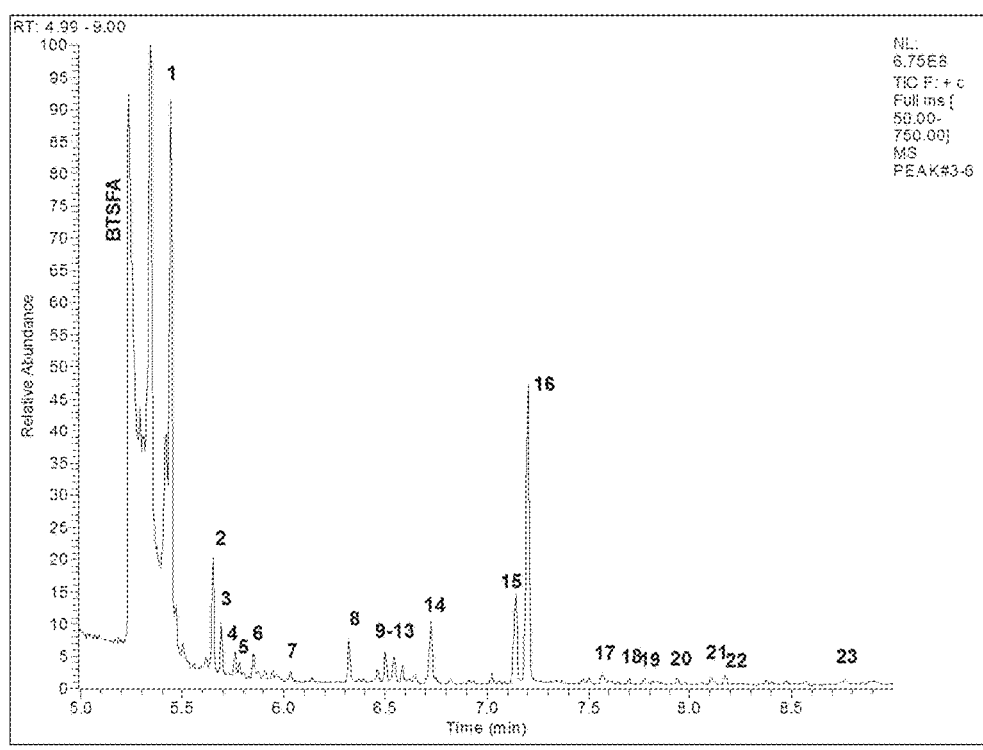
FIG. 2D shows a section of a total ion chromatogram of the pheromone composition of FIG. 2A.
Figure 2E:
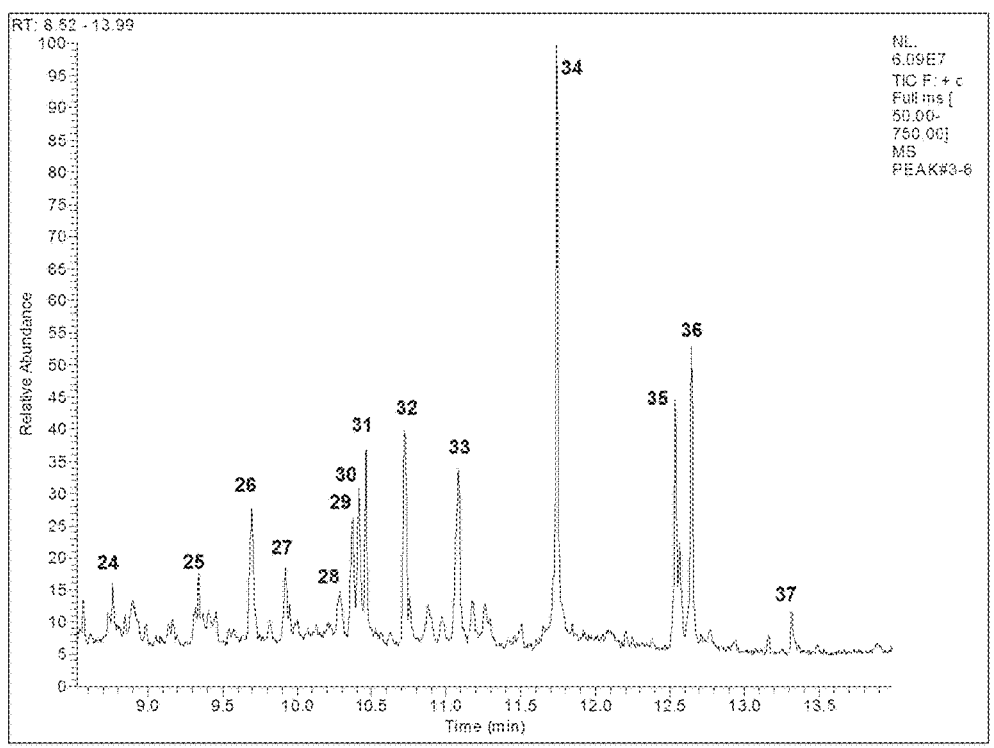
FIG. 2E shows a section of a total ion chromatogram of the pheromone composition of FIG. 2A.

| Components in FIG. 2B-2C | | Components in FIG. 2D-2E | |
| --- | --- | --- | --- |
| Peak No. | Component | Peak No. | Component |
| 1 | dimethyl trisulfide | 1 | ethylamine |
| 2 | undecane | 2 | structure |
| 3 | benzoic acid | 3 | art |
| 4 | artifact | 4 | pyridene |
| 5 | artifact | 5 | art |
| 6 | lauric acid | 6 | 2-methylpropanoic acid |
| 7 | ethyl phthalate | 7 | isopropylphenol tolylsufoxamine |
| 8 | 2-hydroxytetradecanoic acid | 8 | naphalinic species |
| 9 | myristatic acid | 9 | art |
| 10 | 12-methyl-tetradecanoic acid | 10 | phenol acetate species |
| 11 | pentadecanoic acid | 11 | art |
| 12 | palmitoloic acid | 12 | phenol acetate species |
| 13 | palmitic acid | 13 | phenol acetate species |
| 14 | 4-methylhexadecanoic acid | 14 | phenyl acid |
| 15 | heptadecanoic acid | 15 | 2-methylanthracene |
| 16 | linoleic acid | 16 | phosphoric acid |
| 17 | oleic acid | 17 | phenyl acid |
| 18 | methyl oleate | 18 | art |
| 19 | stearic acid | 19 | serine |
| 20 | 9-(o-propylphenyl) nonanoic acid | 20 | threonine |
| 21 | linolenic acid | 21 | hexadecanoic acid-propyl ester |
| 22 | methyl linoleate | 22 | phenolic species |
| 23 | ricinloic acid | 23 | art |
| 24 | 12-hydroxy-9-octadecenoic acid | 24 | adipic acid |
| 25 | eicosanoic acid | 25 | naphthalenic species |
| 26 | methyl eicosanoate | 26 | homocycteine |
| 27 | butyl stearate | 27 | aromatic species |
| 28 | 2-butoxy ethanol phosphate | 28 | cystathionine |
| 29 | heneicosanoic acid | 29 | octandioic acid |
| 30 | docosanoic | 30 | nonandioic acid |
| 31 | phthalate | 31 | azelaic acid |
| 32 | nonacosanoic acid | 32 | butyl amine |
| | | 33 | sorbitol |
| | | 34 | palamitic acid |
| | | 35 | oleic acid |
| | | 36 | stearic acid |
| | | 37 | ricinoleic acid |

Example 3

Figure 3B:
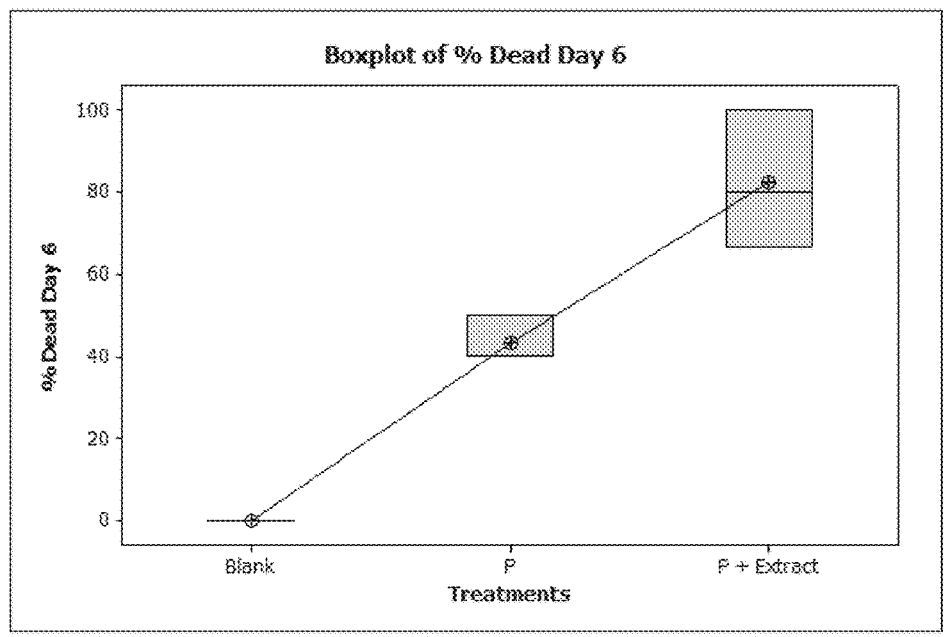
FIG. 3B is a box plot graph showing results of testing the efficacy of a pheromone composition according to an embodiment.

The ability of the extract obtained in Example 1 to increase effectiveness of an insecticide and to increase time spent on an insecticide treated surface was tested. Bed bugs generally avoid resting on insecticide treated surfaces. It was shown in FIG. 3B, displaying the average of four repetitions of the test. In the graph, "P" indicates insecticide alone, and "P+Extract" indicates insecticide and extract.

It was observed that bed bugs spent more than double the time on/under the disk that was treated with insecticide and extract than the disk that was treated with insecticide alone. It was further observed that the mortality rate of the insecticide increased significantly when the insecticide was used in combination with the extract. It was concluded that the efficacy of insecticide treatments could be improved by use of bed bug pheromones.

Example 4

Some of the pheromones extracted as in Example 2 were tested for their effectiveness in attracting bed bugs.

Figure 4A:
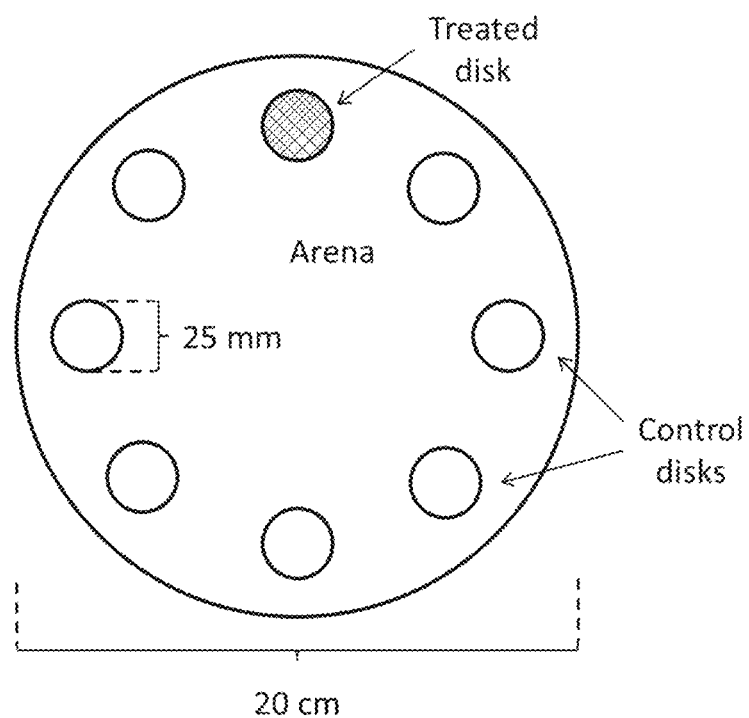
FIG. 4A shows a schematic diagram of a test arena for testing efficacy of pheromone compositions.

Test Arena Set-up: multi-choice assays were performed using 20 cm diameter circular arenas previously described by Olson et al. (2009). Each arena contained eight 25 mm glass microfiber filter disks (Whatman® Grade GF/A, available from GE Healthcare in Piscataway, N.J.): one treated disk and seven control disks that were randomly assigned to eight equally spaced positions around the perimeter of the arena (see FIG. 4A). All disks were adhered to a paper floor (Boise® X-9® multipurpose paper, available from Boise, Inc., in Boise, Id.) by a spot of hot glue (Surebonder, available from FPC Corp., in Wauconda, Ill.), allowing bug entry under the disk. Each disk occupied 12.5% of the total arena floor space (314 cm$^2$). Groups of five males and five females were released into the center of each arena. Replicate arenas (n=6 minimum) were housed side-by-side on a table top under incandescent lighting and standard conditions (25±5° C. and 40%±10% RH). All experiments were started approximately 3 h before the end of the bugs' subjective scotophase. Final positions of bugs were recorded 4 h after release as number under the treated disk (nt), number under the remaining seven control disks (nc), and number elsewhere on the arena floor (nf).

Data Analysis: Arena level aggregation was calculated to measure the bugs' propensity to aggregate under any filter paper disk in the arena, regardless of treatment. Arena level aggregation was indexed by the percentage of released bugs that were under the treated and clean disks compared to the total number of bugs in the arena: Arena level aggregation= (nt+nc)/(nt+nc+nf)×100. Disk-level aggregation was measured to assess the bugs' choice between treated and untreated disks. Disk-level aggregation was calculated as the percentage of bugs that were under the treated disk, compared to the total number of bugs under any disk: Disk-level aggregation=nt/(nt+nc)×100. If the final positions of the bugs were independent of treatment, then mean values for Arena level aggregation and Disk-level aggregation would not be significantly different from 12.5%. Disk-level aggregation values significantly greater than 12.5% would indicate an excess of aggregation at the treated disks, whereas values less than 12.5% would indicate aversion to treated disks. Arena level aggregation and Disk-level aggregation were analyzed as binomial responses using Proc NLMIXED in SAS/STAT® (available from SAS Institute Inc., 2004) to assess main treatment effects and interactions, if appropriate, and to allow for contagion among bugs within each arena. Results were summarized as mean percent 95% confidence intervals for each treatment group, and effects of treatment were tested by significance ($\alpha<0.05$) of coefficients for contrast with the designated reference group.

Figure 4B:
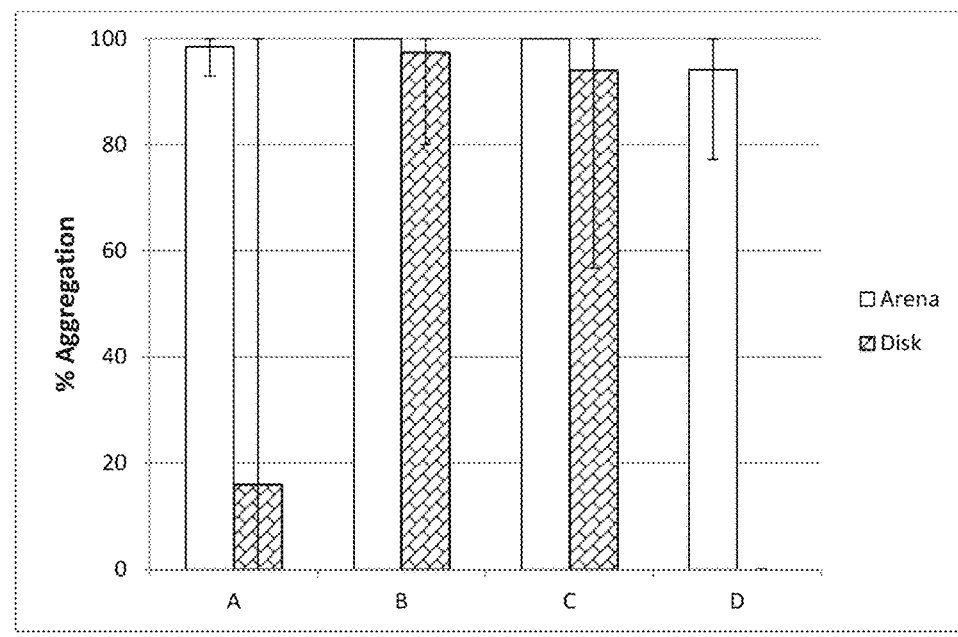
FIG. 4B is a bar graph showing results of testing the efficacy of pheromone compositions according to exemplary embodiments.

Results are shown in a graph in FIG. 4B showing the % arrestment/aggregation to the four combinations of materials. It was observed that about 16% of bed bugs aggregated under the disk with composition A (complete bed bug extract) and 98% remained in the arena; about 97% under the disk with composition B (30 ppm each of TEA, oleamide and urea) and 100% remained in the arena; about 94% under the disk with composition C (30 ppm each TEA, oleamide and octanoic acid) and 100% remained in the arena; and about 0% under the disk with composition D (100 ppm each of TEA, oleamide and octanoic acid) and 94% remained in the arena.

Example 5

Bed bug response to various compositions prepared from synthetic pheromone components was tested. The response to each composition was compared against the extract from bed bug stained papers described in Example 1 and shown in TABLE 1. The concentrations of the individual components were selected to be close to the concentration in the extract. The compositions were prepared with water as the diluent, except for the compositions including octamide, nonamide, and palmitic acid, which were prepared with 3% methanol in water. The formulations (A-G) of the synthetic compositions are shown in TABLE 3.

TABLE 3

Synthetic Compositions

| Formula | Component | Concentration (ppm) |
|---|---|---|
| A | MDEA | 4 |
|   | Bicine | 1 |
|   | TEA | 17 |
|   | Octamide | 1 |
|   | Palmitic Acid | 1 |
|   | Nonamide | 1 |
| B | Bicine | 1 |
|   | TEA | 17 |
|   | Octamide | 1 |
|   | Palmitic Acid | 1 |
|   | Nonamide | 1 |
| C | Bicine | 1 |
|   | TEA | 17 |
| D | Octamide | 1 |
|   | Palmitic Acid | 1 |
|   | Nonamide | 1 |
| E | DMTS | 1 |
| F | MDEA | 4 |
| G | DMTS | 1 |
|   | MDEA | 4 |

Figure 5A:
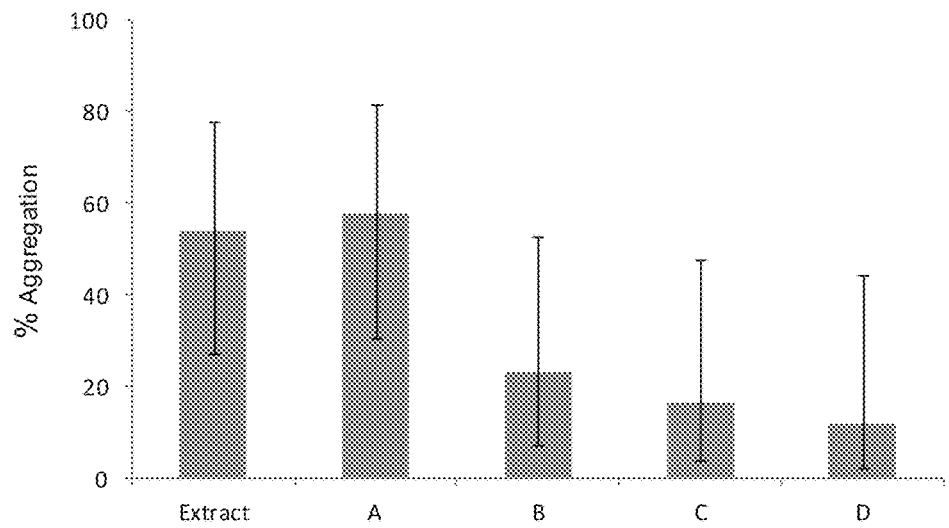
FIG. 5A is a bar graph showing results of testing the efficacy of pheromone compositions according to exemplary embodiments.
Figure 5B:
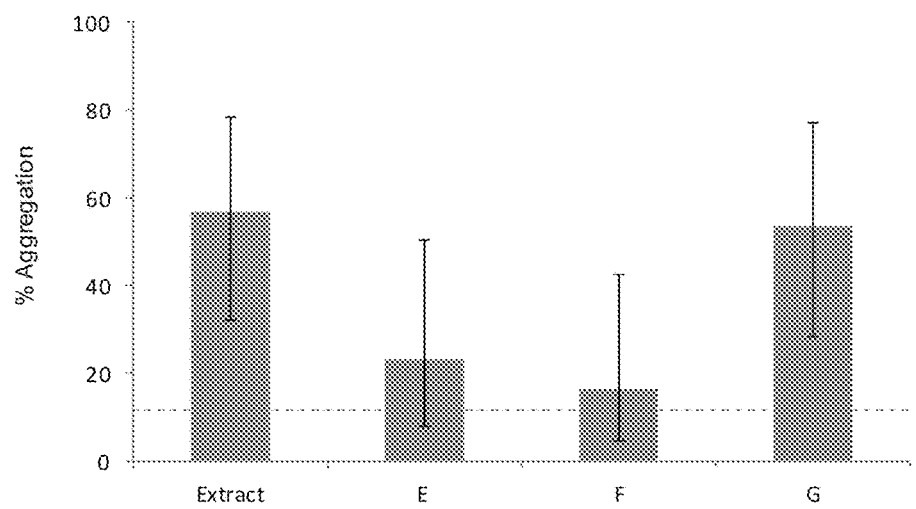
FIG. 5B is a bar graph showing results of testing the efficacy of pheromone compositions according to exemplary embodiments.

Bed bug response was measured as %-aggregation under fiber disks treated with the compositions as described in Example 4. Each composition was tested 17 times (n=17). The results are shown in FIGS. 5A (compositions A-D) and 5B (compositions E-G). In the bar graphs, the error bars indicate 95% confidence intervals.

It was observed that compositions A and G elicited the strongest responses. It was further observed that MDEA in combination with one or more other pheromone components produces a strong aggregation reaction.

Example 6

Bed bug response to various combinations of DMTS, MDEA, histamine, TEA, and alkanolamine prepared from synthetic pheromone components was tested. The response to each composition was compared against the extract from bed bug stained papers described in Example 1 and shown in TABLE 1.

The compositions were prepared with water as the diluent, except for the compositions including alkanolamine, which were prepared with 3% methanol in water. The formulations (H-R) of the synthetic compositions are shown in TABLE 4.

TABLE 4

Synthetic Compositions

| Formula | Component | Concentration (ppm) |
|---|---|---|
| H | DMTS | 1 |
| J | MDEA | 2 |
| K | MDEA | 2 |
|   | DMTS | 1 |
| L | Histamine ("Hist") | 2 |
| M | Histamine | 2 |
|   | DMTS | 1 |
| N | TEA | 2 |
| P | TEA | 2 |
|   | DMTS | 1 |
| Q | Alkanolamine ("Alk") | 1 |
| R | Alkanolamine ("Alk") | 2 |
|   | DMTS | 1 |

Figure 6:
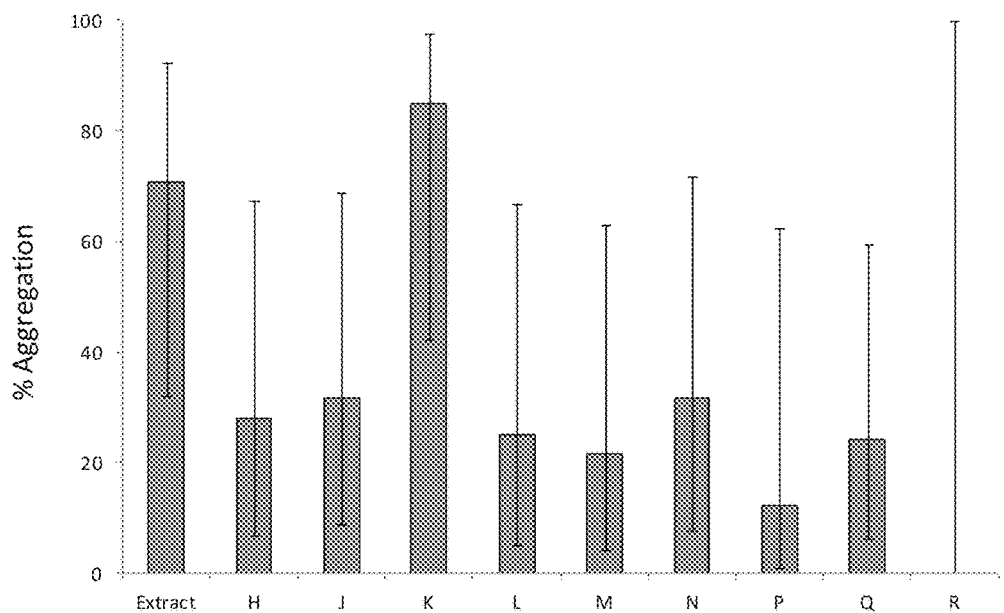
FIG. 6 is a bar graph showing results of testing the efficacy of pheromone compositions according to exemplary embodiments.

Bed bug response was measured as %-aggregation under fiber disks treated with the compositions as described in Example 4. Each composition was tested 6 times (n=6). The results are shown in FIG. 6. In the bar graphs, the error bars indicate 95% confidence intervals.

It was observed that composition K (2 ppm MDEA and 1 ppm DMTS) elicited the strongest response. It was further observed that DMTS and MDEA exhibited a synergistic effect.

Example 7

Bed bug response to various concentrations of MDEA in combination DMTS prepared from synthetic pheromone components. In each composition, the level of DMTS was held at 1 ppm, but the level of MDEA was varied from 0.4 ppm to 4 ppm, 40 ppm, and 400 ppm. A composition prepared from analytical grade purity (99.99%) DMTS was also tested at 1 ppm DMTS (indicated as "DMTS pure" in FIG. 7) and 4 ppm MDEA. The other compositions were prepared from a 98% purity stock of DMTS.

Figure 7:
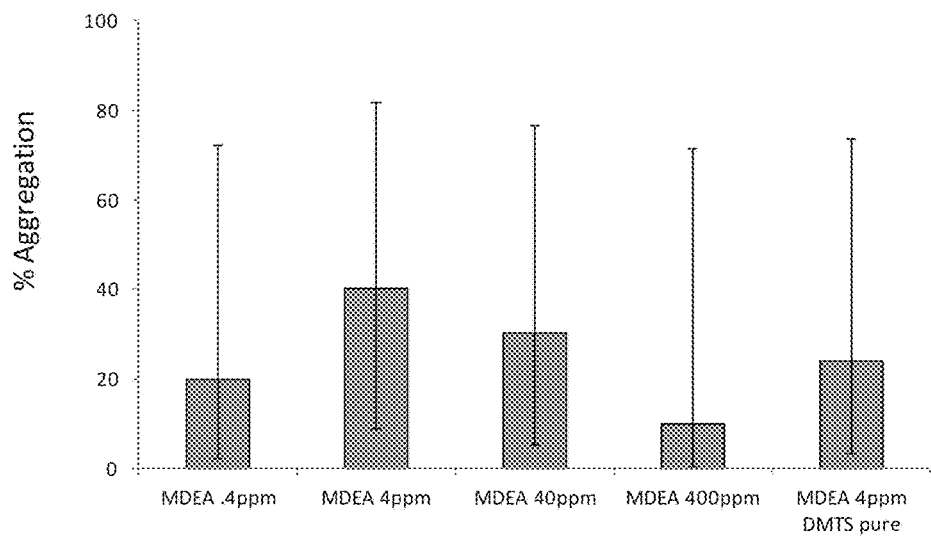
FIG. 7 is a bar graph showing results of testing the efficacy of pheromone compositions according to exemplary embodiments.

Bed bug response was measured as %-aggregation under fiber disks treated with the compositions as described in Example 4. Each composition was tested 5 times (n=5). The results are shown in FIG. 7. In the bar graphs, the error bars indicate 95% confidence intervals.

It was observed that the strongest response for MDEA and 1 ppm DMTS occurs between the concentrations of 0.4 ppm and 400 ppm MDEA, most likely between the concentrations of 0.4 ppm and 40 ppm MDEA.

Example 8

Effectiveness of insecticide in combination with synthetic pheromone components and extract obtained in Example 1 to kill bed bugs or affect their feeding status and egg oviposition was tested.

Test Arena Set-up: the assays were performed using 20 cm diameter circular arenas. Each arena contained two tent-shaped filter paper harborages attached to the arena about 10 cm apart using hot glue. In each test, the underside of the harborage was treated 24 hours prior to the test.

The insecticide used was Temprid®. The treatments were as follows:
Control: 4 ppm MDEA and 1 ppm DMTS (denoted Standard "S")
Treatment 1: Insecticide only (denoted "T")
Treatment 2: Insecticide and Extract (denoted "TE")
Treatment 3: Insecticide, 4 ppm MDEA and 1 ppm DMTS (denoted "TS")

In each test run, one harborage was treated and the other one untreated. Ten bed bugs were used per arena. The bed bugs were allowed to acclimate to the arenas for 10 minutes prior to their release. Upon release, the bed bugs were allowed to move freely around the arena with two harborage areas on each arena. After one hour of exposure inside the arenas, the bed bugs were relocated to a recovery container with a clean filter paper.

Mortality was examined at 24 hr, 48 hr, 72 hr, 5 days and 1 week post-exposure. Bed bugs were recorded as dead if there was no movement when probed with tweezers, or moribund if they were probed and there was movement, but they were unable to right themselves or cling to the filter paper in the recovery containers. One week post-exposure the bed bugs were allowed to feed from the artificial feeding system for 10 minutes and the number of fully engorged bugs was recorded. In addition, the number of eggs deposited on the filter paper in the recovery container was quantified and recorded one week post-exposure.

Figure 8A:
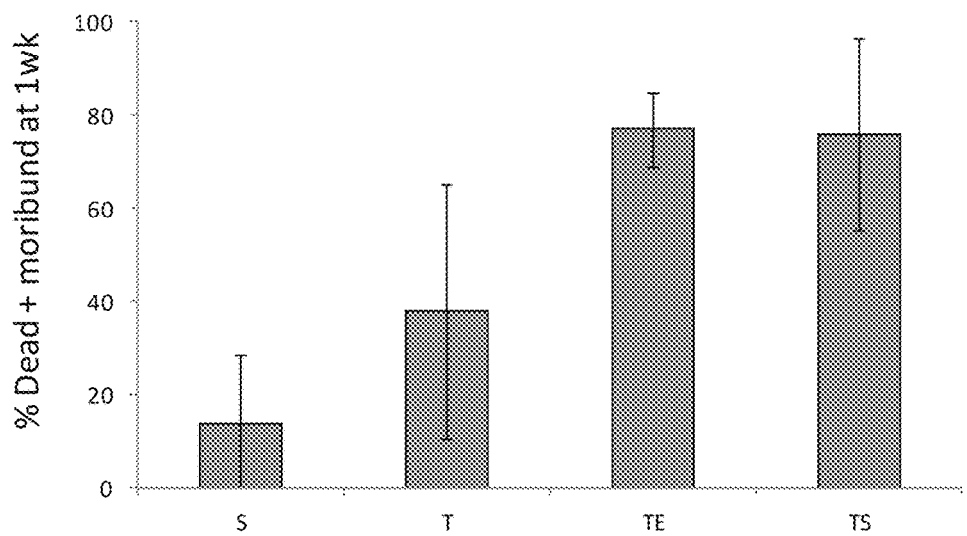
FIG. 8A is a bar graph showing results of testing the efficacy of insecticide with a pheromone composition according to an embodiment.
Figure 8B:
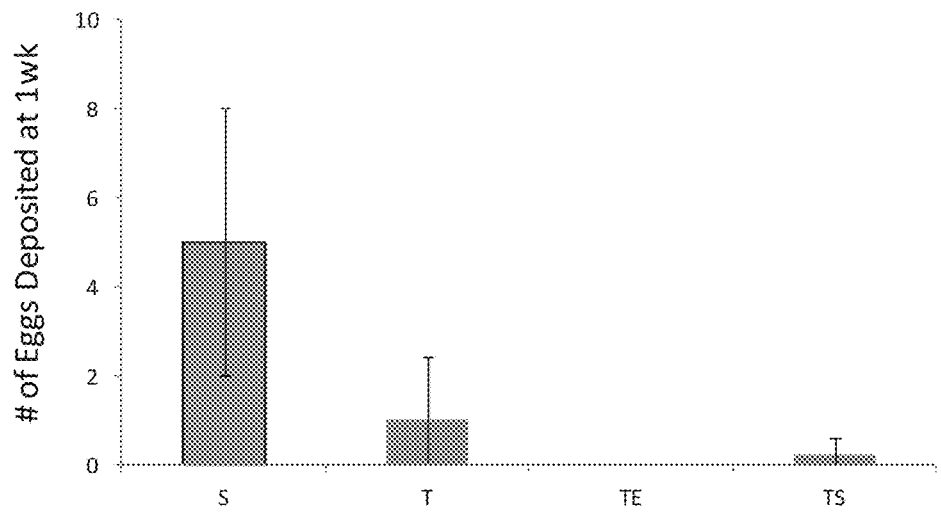
FIG. 8B is a bar graph showing results of testing the efficacy of insecticide with a pheromone composition according to an embodiment.
Figure 8C:
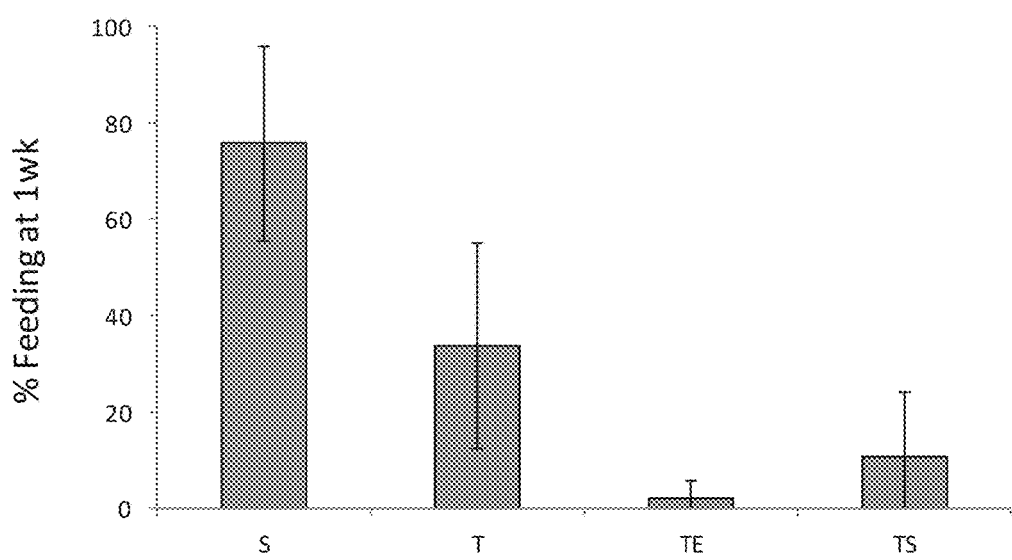
FIG. 8C is a bar graph showing results of testing the efficacy of insecticide with a pheromone composition according to an embodiment.

The results are shown in FIGS. 8A-8C. FIG. 8A shows the percent of dead and moribund bed bugs at one week post-exposure, FIG. 8B shows the number of eggs deposited, and FIG. 8C shows the percentage of bed bugs that fed one week post-exposure.

It was observed that the effectiveness of the insecticide improved by using the insecticide in conjunction with the pheromone extract or with 4 ppm MDEA and 1 ppm DMTS. Improvements were observed both in the dead/moribund data, as well as the reduction in number of eggs laid and the feeding behavior.

While certain embodiments of the invention have been described, other embodiments may exist. While the specification includes a detailed description, the invention's scope is indicated by the following claims. The specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A composition for attracting bed bugs comprising:
    methyl diethanolamine (MDEA), and dimethyl trisulfide (DMTS);
    an insecticide that is effective against bed bugs;
    a carrier; and
    optionally one or more additives selected from oleamide, octanamide, nonanamide, and laurylamide; urea, biuret, and triuret; and one or more aliphatic fatty acids.

2. The composition of claim 1 further comprising a surfactant.

3. The composition of claim 1 comprising 0.1-30 ppm MDEA.

4. The composition of claim 1 wherein the total concentration of a mixture of components selected from MDEA, DMTS, oleamide, octanamide, nonanamide, laurylamide, urea, biuret, triuret, and aliphatic fatty acids is between 1-100 ppm.

5. A method for treating an article comprising applying the composition of claim 1 to the article.

6. The method of claim 5, wherein the article comprises a device for trapping or detecting bed bugs.

7. The method of claim 5, wherein the article comprises a device for treating a bed bug infestation.

8. The method of claim 5, wherein the composition is applied to the surface of the article.

9. The method of claim 5, wherein the composition is impregnated into the article.

10. A method for treating an area infested with bed bugs, the method comprising:
   (a) applying a primary treatment to the area;
   (b) applying a secondary treatment to the area,
   wherein the primary treatment comprises methyl diethanolamine (MDEA), and dimethyl trisulfide (DMTS); and optionally one or more additives selected from the group consisting of oleamide, octanamide, nonanamide, laurylamide, urea, biuret, triuret, one or more aliphatic fatty acids, and mixtures thereof, and
   wherein the secondary treatment kills bed bugs.

11. The method of claim 10, wherein the bed bugs comprise adult bed bugs and nymphs.

12. The method of claim 10, wherein the secondary treatment comprises application of an insecticide.

13. The method of claim 10, wherein the secondary treatment comprises application of heat.

14. The method of claim 10, wherein the primary treatment and secondary treatment are applied consecutively.

15. The method of claim 10, wherein the primary treatment and secondary treatment are applied simultaneously.

16. The method of claim 10, wherein the secondary treatment is applied 10-240 minutes after the primary treatment.

17. The method of claim 10, wherein the secondary treatment is repeated.

18. The method of claim 10, wherein the primary treatment further comprises additional bed bug pheromones.

19. The method of claim 10, wherein applying the primary treatment comprises applying from $5.0 \times 10^{-6}$ µg/cm$^2$ to about $1.5 \times 10^{-2}$ µg/cm$^2$ of pheromone components to the area.

20. The method of claim 10, wherein applying the primary treatment comprises applying from about $1 \times 10^{-5}$ µg/cm$^2$ to about $2.5 \times 10^{-3}$ µg/cm$^2$ of pheromone components to the area.

21. A trap for capturing insects, the trap comprising:
   (a) a housing comprising one or more openings;
   (b) a receiving area;
   (c) an attractant component comprising a pheromone composition, the pheromone composition comprising methyl diethanolamine (MDEA), and dimethyl trisulfide (DMTS), and optionally one or more amides selected from oleamide, octanamide, nonanamide, and laurylamide; urea, biuret, and triuret; and one or more aliphatic fatty acids; and
   (d) an insecticide that is effective against bed bugs.

22. A method for treating an area that is at risk of contamination with bed bugs, the method comprising applying a treatment to the area, wherein the treatment comprises:
   (a) a pheromone composition comprising methyl diethanolamine (MDEA), and dimethyl trisulfide (DMTS); and optionally one or more additives selected from the group consisting of oleamide, octanamide, nonanamide, laurylamide, urea, biuret, triuret, one or more aliphatic fatty acids, and mixtures thereof; and
   (b) an insecticide that is effective against bed bugs.

23. The method of claim 22, wherein the treatment remains effective against bed bugs for at least two weeks after application.

24. The method of claim 22, wherein the bed bugs comprise adult bed bugs and nymphs.

25. The method of claim 22, further comprising applying heat to the area.

26. The method of claim 22, wherein the pheromone composition and insecticide are applied consecutively.

27. The method of claim 26, wherein the insecticide is applied 10-240 minutes after the pheromone composition.

28. The method of claim 26, wherein the insecticide treatment is repeated.

29. The method of claim 22, wherein the pheromone composition and insecticide are applied simultaneously.

30. The method of claim 22, wherein the pheromone composition and insecticide are applied as part of a single composition.

31. The method of claim 22, wherein the pheromone composition further comprises other bed bug pheromones.

32. The method of claim 22, wherein applying the pheromone composition to the area comprises applying from $5.0 \times 10^{-6}$ µg/cm$^2$ to about $1.5 \times 10^{-2}$ µg/cm$^2$ of pheromone components to the area.

33. The method of claim 22, wherein applying the pheromone composition comprises applying from about $1 \times 10^{-5}$ µg/cm$^2$ to about $2.5 \times 10^{-3}$ µg/cm$^2$ of pheromone components to the area.

* * * * *